United States Patent [19]

Tamari

[11] Patent Number: 4,650,471
[45] Date of Patent: Mar. 17, 1987

[54] FLOW REGULATING DEVICE FOR PERISTALITIC PUMPS

[76] Inventor: Yehuda Tamari, 12 Pond View Dr., Syosset, N.Y. 11791

[21] Appl. No.: 572,697

[22] Filed: Jan. 20, 1984

[51] Int. Cl.$^4$ ............... A61M 1/00; A61M 37/00; A61M 11/00; F04B 43/08
[52] U.S. Cl. ................... 604/153; 604/132; 604/133; 604/93; 604/118; 417/474; 417/475; 417/476; 417/477; 138/119; 138/114
[58] Field of Search ............... 604/132, 133, 93, 153, 604/118; 417/474–477, ; 138/119, 114

[56] References Cited

U.S. PATENT DOCUMENTS

| | | | |
|---|---|---|---|
| 2,928,353 | 3/1960 | Murray | 417/475 |
| 3,105,447 | 10/1963 | Ruppert | 417/477 |
| 3,192,863 | 3/1962 | Vadot | 103/149 |
| 4,290,736 | 9/1981 | Bernasconi | 138/114 X |
| 4,515,536 | 5/1985 | Van Os | 417/474 X |
| 4,515,589 | 5/1985 | Austin et al. | 604/122 |

FOREIGN PATENT DOCUMENTS

M 21958  7/1956  Fed. Rep. of Germany ........ 138/63

OTHER PUBLICATIONS

Article on Artificial Kidney Use of Floodpump Bio-Medical Engineering Dept. Genie Medical 41 Ave. Geo. V Paris 84.

Mannual on Artificial Organs vol. II, Yukihiko Nose, C. V. Mosby Co. 1973.
Proceedings of the American Academy of Cardiovascular Perfusion, vol. 4, Jan. 1983.
Correspondence Between Applicant and Johnson & Johnson, Subject: Non-Enabling Embodiment of Present Invention.

*Primary Examiner*—Andrew H. Metz
*Assistant Examiner*—William G. Wright
*Attorney, Agent, or Firm*—Jonathan B. Schafrann

[57] ABSTRACT

The present invention provides a pumping chamber to be constructed as follows:

A collapsible tubing is attached to an inlet fitting and to and outlet fitting to transport a biologic fluid such as blood therethrough. An outer tubing surrounds the collapsible tubing and is secured to the outer surface of the inlet fitting and to the outer surface of the outlet fitting, forming a chamber thereby. At least a duality of ports defining passageways through the wall of the outer tubing permits communication of the chamber with ambient conditions outside the chamber. The ports are designed to accept such devices as pressure gauges, alarm systems and devices to regulate intrachamber pressure, to observe arterial pressure, and to regulate collapse and occlusion of collapsible tubing in response to inadequate blood volumes.

16 Claims, 5 Drawing Figures

FLOW REGULATING DEVICE FOR PERISTALITIC PUMPS

BACKGROUND AND SUMMARY OF THE INVENTION

1. Technical Field

The present invention appertains generally to extracorporeal pumps, and more specifically to a pumping chamber for an extracorporeal pumping device.

There are a number of medical procedures which require that the pumping duties of the human heart be circumvented, and that these duties be assumed by mechanical means. While there are many available pumps, the best-known types utilize one or more rollers and a length of tubing termed the pumping chamber which carries the blood. Typically, as the rollers of the mechanical pump squeeze the tubing or pumping chamber shut, blood or other biologic fluid is transported through the tubing and is eventually returned to the patient. During many medical procedures such as coronary by-pass-type surgery, prolonged extracorporeal pumping is necessary.

The above-described roller-single tube pumping devices present recognized dangers to the patient. These pumping devices which possess pumping chambers composed of single tubing elements tend to "run dry," that is, to continue pumping even when no blood is being transported therethrough. The reason for this phenomenon is that the single tube of the standard pumping chamber has great mechanical strength, necessary to absorb and recover from the constant shock of the roller assembly; decreased pressure within the tube caused by the absence of blood is not sufficient to overcome the mechanical strength of the tubing, cause its collapse, and cease the pumping action. With presently available devices, inadequate blood volumes result in the formation of a suction through continued pumping, exposing the patient to the possible introduction of an air embolism or the dangers of negative flow.

Heretofore, solutions to the above-stated problems have remained elusive, underscoring the longstanding need for an extracorporeal pumping device that responds to inadequate blood flow rates. The instant invention presents the user with an alternate pumping chamber to be used in a roller-type devices which enables the user to read changes in the patient's blood pressure and to utilize a pumping device that occludes in the presence of inadequate blood volume.

2. Prior Art

The prior art relating to extracorporeal pumping devices is primarily composed of many devices which rely on rollers and single-tube pumping chambers. As stated hereinabove, such devices suffer from well-recognized deficiencies which may cause harm to the patient. Recently, Austin et al. (U.S. Pat. No. 4,515,589) have modified the standard single-tube perfusion loop or single-tube pumping chamber by making a pumping section comprised of a thin-walled inner tube positioned in a thick-walled outer tube, the annular space created by the overlay being vented to the atmosphere. It is further disclosed, that the inner tube will collapse in response to inadequate volumes of blood, the collapse pressure of the inner tube being predicated upon atmospheric pressure.

SUMMARY OF THE INVENTION

Accordingly, the present invention is constructed as follows. A collapsible tubing fashioned from an elastomeric material is connected to an inlet fitting and to an outlet fitting, thus forming a conduit to carry biologic fluid therethrough. Blood fills the collapsible tubing after entering through the inlet. The blood is squeezed along the collapsible tubing by a roller assembly of the mechanical pump, and exits via the outlet fitting. The collapsible tubing is designed to occlude at a set pressure which may be modified as described hereinbelow. An outer tubing surrounds the collapsible tubing, and is attached to the outer surface of the outlet fitting at the most downstream boundary. The outer tubing is of greater mechanical strength than the collapsible tubing, possessing a thicker wall diameter than that of collapsible tubing. The overlay of outer tubing secured over collapsible tubing creates a chamber. The outer tubing possesses at least two ports, defining passageways through the wall of the outer tubing so that the environment within the chamber is in total communication with ambient conditions. The ports are located in downstream relation to each other and may be maintained in an open or unblocked condition so that the pressure influencing occlusion will closely approximate atmospheric pressure. The ports may be fitted with a pressure-modifying device so that the pressure within the chamber may be decreased by evacuating air or increased by injecting a gas or a fluid. The collapsible tubing is designed to fully occlude at a set pressure which may be modified by increasing or decreasing intrachamber pressure. Moreover, by either pressurizing or evacuating the chamber and by disposing a pressure gauge within a port, slight changes of a patient's venous pressure may be detected. By virtue of this invention, an accurate appraisal of a patient's blood pressure response to the trauma of surgery can be obtained.

Therefore, while the foregoing presents a general description of the present invention, other objects and advantages will be apparent from the detailed description and the accompanying drawings.

DETAILED DESCRIPTION

Figure 1:
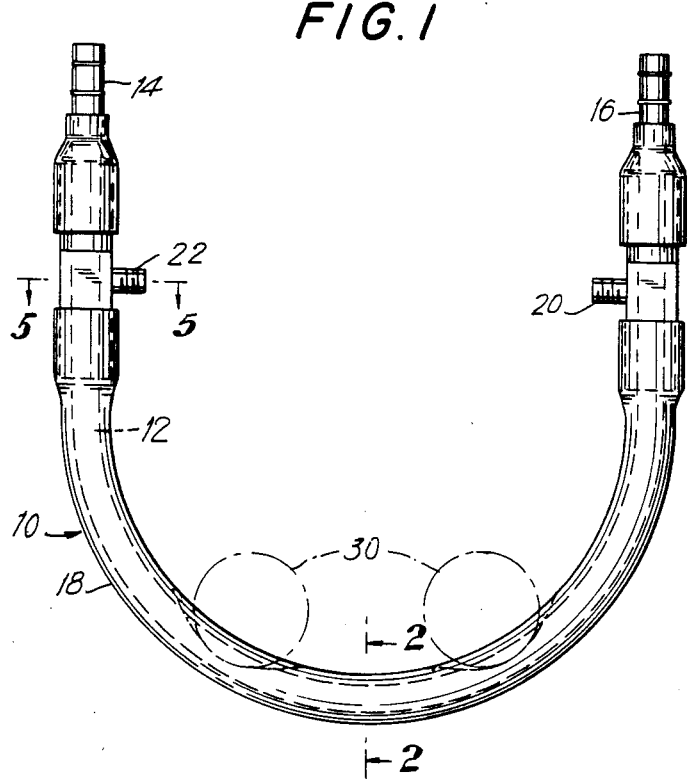
FIG. 1 is an elevational view of the pumping chamber showing a roller squeezing blood therethrough.
Figure 4:
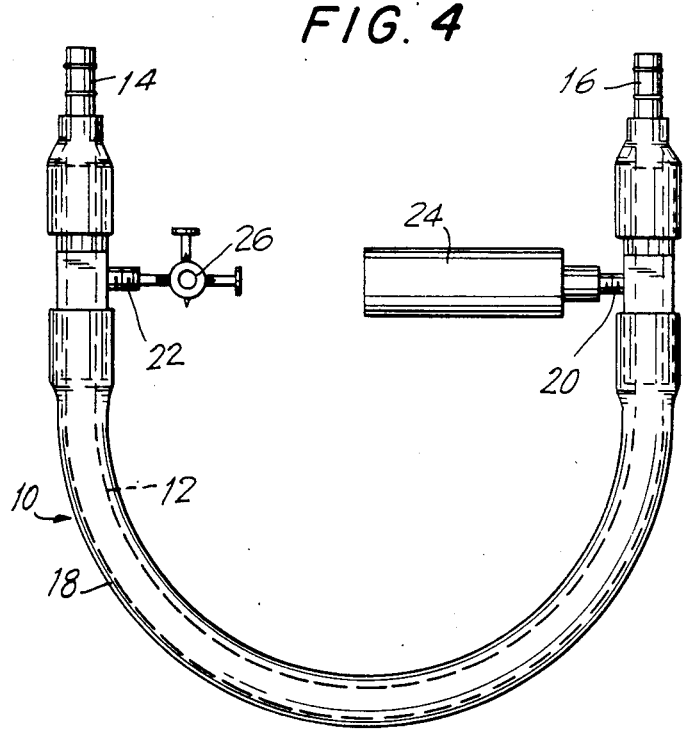
FIG. 4 is an elevational view showing a cutaway view of the downstream port, a pressure-modifying device in said port, and a device adapted to accept further accessories in the upstream port.

Set out hereinbelow are the preferred embodiments of the pumping chamber for extracorporeal pumping devices, the pumping chamber of the present invention to be generally referred to by numeral 10. The preferred embodiments are illustrated in FIGS. 1 and 4, with FIG. 4 representing the most preferred embodiment. Pumping chamber 10 of FIG. 4 utilizes the basic structure of FIG. 1, with additional elements described hereinbelow.

FIG. 1 shows pumping chamber 10 without modification. This embodiment contains a collapsible tubing, set out in dotted lines in FIG. 1, said tubing being attached to inlet fitting 14 at its most upstream boundary. Collapsible tubing 12 in dotted lines is attached to outlet fitting 16 at its most downstream boundary. Blood or other biologic fluids enter inlet fitting 14, transverse or flow through collapsible tubing 12, and exit from pumping chamber 10 through outlet fitting 16. Inlet and outlet fittings 14 and 16 should be fashioned from a rigid hydrophobic biocompatible polymer.

Figure 2:
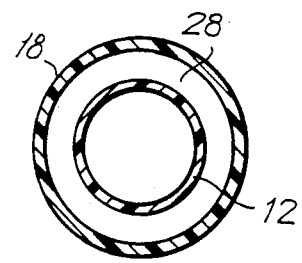
FIG. 2 is a sectional view taken along lines 2—2 of FIG. 1, showing the collapsible tubing in a non-occluded condition.

Collapsible tubing 12 is the conduit for transporting blood through pumping chamber 10, and is designed to possess little mechanical strength. This tubing will collapse at a predesignated pressure which could be set as desired by the user. FIG. 2 shows tubing 12 in an open condition, representing the tube in a filled state, and in an occluded condition according to FIG. 3 wherein inadequate blood volumes have caused the tube to collapse.

Collapsible tubing 12 may be fashioned from a variety of elastomeric materials. The preferred material must be either biocompatible or be amenable to being coated with a biocompatible substance such as albumin. In addition, the material must have rubber-like flexibility and not be brittle at ambient temperatures and elevated or lowered pressures. The material must be hydrophobic so that it will not absorb the biologic fluid, and it must be resilient so that it will expand and contract over the prolonged periods common to procedures such as dialysis or by-pass operations. The preferred material for collapsible tubing 12 is polyurethane, although a polymer such as silicone rubber may be used. A seamless polyurethane tube of from 0.007 inches to 0.03 inches in thickness is preferred, while a wall thickness of from 0.009 to 0.015 is most preferred. (Until recently, materials such as polyurethane or other polymers were not available for seamless tubes).

Surrounding collapsible tubing 12 is outer tubing 18. Although outer tubing 18 surrounds collapsible tubing 12, it is not continuous with the passage through inlet fitting 14 or outlet fitting 16. Instead, outer tubing 18 is secured to the outer surface of inlet fitting 14 and outlet fitting 16, thereby creating chamber 28. The area of the chamber is defined as the difference between the inside diameter of outer tubing 18 and the outer diameter of collapsible tubing 12. Outer tubing 18 is to be constructed from a polymer possessing greater mechanical strength than that of collapsible tubing 12. Outer tubing 18 does not have to be biocompatible, but must act as a cushion or barrier to protect the collapsible tubing 12 from the repeated battering caused by the roller of the mechanical device. In furtherance of this protective roll, outer tubing 18 must be resilient and able to return to its resting shape, acting as a guide to maintain the loop-shape within the roller device. The preferred material for outer tubing 18 is polyvinyl chloride, although silastic rubber or other polymers may be used. As with tubing 12, tubing 18 must be flexible and not become brittle at the prescribed temperatures and pressures. It has been found that a polyvinyl chloride tubing possessing a wall thickness of from 0.0625 (1/6) inches to 0.1562 (5/32) inches is most preferred. Other materials may of course be used with concomitant increase or decrease in wall diameter being required.

Figure 3:
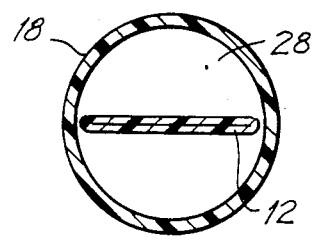
FIG. 3 is a sectional view taken along lines 2—2 of FIG. 1, showing the collapsible tube in an occluded condition.

As one can see in FIGS. 2 and 3, the outer tubing 18 possesses a wall diameter which is greater than collapsible tubing 12. As a preferred embodiment, the outside diameter of the collapsible tubing 12 will always be less than the inside diameter of the outer tubing, so that the space defined by chamber 28 is maintained therein. As illustrated, collapsible tubing 12 may be collapsed in an occluded attitude or swollen with blood without affecting the condition of outer tubing 18.

Figure 5:
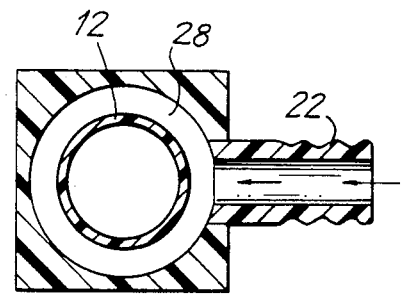
FIG. 5 is a sectional view taken along lines 5—5 of FIG. 1, of a port describing a passageway through the outer tubing.

FIG. 1 also shows an upstream port 22 and a downstream port 20 which create a passageway through the wall of outer tube 18, as shown more clearly in FIG. 5. The passageways described by ports 20 and 22 allow chamber 28 to communicate directly with ambient conditions. Therefore, when ports 20 and 22 are in an unblocked condition, the pressure acting against collapsible tubing 12 most closely approximates atmospheric pressure.

Collapsible tubing 12 is designed to collapse at a set pressure. For purposes of the instant invention, the definition of set pressure is the pressure at which collapsible tubing 12 collapses and occludes. The set pressure may be calculated as the difference between the pressure within chamber 28 and the elasticity of the polymeric elastomer from which collapsible tubing 12 is fashioned. When the pressure within chamber 28 pushes against the outside wall of collapsible tubing 12 and exceeds the pressure within collapsible tubing 12 of the blood pushing outwardly and maintaining said tubing in an open condition, collapsible tubing 12 collapses and occludes. When used in existing roller devices the present invention (comprised of a polyvinyl outer tubing and a seamless polyurethane collapsible tubing) can generate flow rates of between 0.05–5 liters per minute with a change in filling pressure over the set pressure of from 0–20 torr., showing the flexibility of the pumping chamber. By modifying the pressure within chamber 28 which acts upon collapsible tubing 12, the set pressure which causes the collapse of said tubing 12 changes. The user may adjust the pressure within chamber 28 so that the set pressure is either above or below atmospheric pressure.

FIG. 4 illustrates pumping chamber 10 with a pressure-modifying device 24 occupying port 20, and a second device 26 occupying port 22 and sealing chamber 28. Port 22 can accept devices such as pressure gauges or tubing assemblies. A simple Y-shaped tubing assembly could join port 20 with port 22, permitting positive pressure or negative pressure to be introduced simultaneously to both the upstream and downstream sections of chamber 28. By introducing positive or negative pressure in both ports, it would be difficult for collapsible tubing 12 to isolate a chamber section in the unlikely event that said tubing expands past its expected limits. Pressure-modifying device 24 may be a simple accessory such as a syringe with a lockable plunger. With such a device, one could inject a desired amount of air or other gas into chamber 28 or withdraw a specific volume of air or other gas from chamber 28. More preferably, pressure-modifying device 24 should be composed of a rigid chamber wherein pressure could be generated or evacuated by a bulb-type assembly.

A variety of devices may be operatively disposed within port 22. For example, a pressure gauge can be attached to an alram system so that the operating team can be warned in the event of a fall in the patient's venous pressure. This invention permits the monitoring of blood pressure during a surgical procedure whereby the human heart has been by-passed. This monitoring applies to even slight decreases in blood pressure. Early detection of a drop in venous pressure allows the operating team to react to and correct the problem, sparing the patient from complete arterial collapse. If blood volumes drop too quickly to be corrected, collapsible tubing 12 of pumping chamber 10 occludes, preventing the introduction of an air embolism or negative flow. Unlike the present invention, currently available pumping devices would continue to pump in the absence of blood flow.

Chamber 28, which is created by outer tubing 18 surrounding collapsible tubing 12, may be filled with a variety of media. For example, a liquid could be instilled in or circulated through chamber 28 via ports 20 and 22. A variety of gases such as nitrogen, helium or carbon dioxide could be installed within said chamber. Each medium affects the set pressure differently, thus allowing the user an almost infinite number of possible set pressures.

By sealing port 20 with a pressure gauge, one can increase or decrease the pressure within chamber 28 by either pumping air into the chamber or evacuating air from the chamber. (The outer tubing, which is preferably constructed from polyvinyl chloride, would possess a wall thickness which is adequate for the pressures generated therein). Therefore, a slightly positive pressure within chamber 28 would change the set pressure so that a decrease in blood flow therethrough lesser than the requisite decrease at atmospheric pressure would cause the collapse of collapsible tubing 12. In the alternative, a slightly negative pressure within chamber 28 pursuant to the evacuation of air from the chamber would require a greater decrease in blood flow in order to cause collapsible tubing 12 to occlude.

In order to utilize the instant invention, one must attach chamber 10 to a roller-type mechanical device as above-described but not claimed herein. According to the present invention, the pumping chamber is designed to conform to the familiar loop-shape as required by such roller-pump devices. Blood enters inlet 14 and fills collapsible tubing 12. As illustrated in FIG. 1, roller 30 squeezes outer tubing 18 which, in turn, squeezes collapsible tubing 12, propelling the blood along the length of collapsible tubing 12. The blood exits or is squeezed from collapsible tubing 12 through outlet 16. (Inlet and outlet fittings 14 and 16 are to be constructed from a biocompatible rigid hydrophobic thermoplastic polymer). Throughout this pumping period, the pressure in chamber 28 remains constant. As outer tubing 18 and collapsible tubing 12 recover from the results of the squeezing actions of roller assembly 30, collapsible tubing 12 refills with blood and outer tubing 18 returns to its rounded conformation. This basic procedure will be repeated for the entire time the human heart is by-passed.

While the various embodiments described herein may utilize materials such as polyurethane and polyvinyl chloride, it is understood by one skilled in the art that many other thermoplastic polymers can be substituted therefor.

I claim:

1. A pumping chamber for an extracorporeal pumping device comprising:
   a. a collapsible tubing attached to an inlet means and to an outlet means, said collapsible tubing being capable of transporting blood from said inlet to said outlet;
   b. an outer tubing surrounding said collapsible tubing, said outer tubing being secured to the outermost boundary of said inlet means and said outlet means and defining a chamber wherein said collapsible tubing is longitudinally disposed therethrough;
   c. at least a duality of ports located in downstream relation one to the other, said ports being situated within said outer tubing and defining a passsageway therethrough; and
   d. at least a pressure modifying device effective for producing positive or negative pressure being disposed in on one of said ports and such other devices disposed within the remaining ports.

2. A collapsible tubing according to claim 1 wherein said collapsible tubing is constructed from a thermoplastic elastomer.

3. A collapsible tubing according to claim 1 wherein said collapsible tubing is constructed from polyurethane.

4. A collapsible tubing according to claim 1 wherein said collapsible tubing is a seamless polyrethane tubing possessing a wall thickness of from 0.009 inches to 0.015 inches.

5. An inlet means and an outlet means according to claim 1 wherein said means are constructed from a rigid hydrophobic biocompatible polymer.

6. An outer tubing according to claim 1 wherein said outer tubing is constructed from a thermoplastic polymer.

7. An outer tubing according to claim 1 wherein said tubing is a polyvinyl chloride tubing possessing a wall thickness of from 0.0625 to 0.1562 inches.

8. At least a duality of ports according to claim 1 wherein said ports are constructed from a rigid hydrophobic polymer.

9. A pumping chamber for an extracorporeal pumping device according to claim 1 wherein a pressure-modifying device effective for producing positive or negative pressure is disposed within one of said ports and a second device is disposed within the remaining port.

10. A pressure-modifying device according to claim 9 wherein said device is capable of introducing a fluid or gas within said chamber.

11. A pressure-modifying device according to claim 9 wherein said device is further comprised of a rigid chamber and a secondary source for generating positive or negative pressures.

12. A second device according to claim 9 wherein said device is a pressure gauge.

13. A second device according to claim 9 wherein said device is an alarm system to advise a user of inadequate blood flow.

14. A collapsible tubing according to claim 1 wherein said tubing collapses and occludes when the chamber pressure exceeds the set pressure within said collapsible tubing.

15. A method for decreasing the set pressure of collapsible tubing comprising the steps of:
   a. isolating the chamber as defined by outer tubing surrounding and being secured over collapsible tubing, from ambient pressure;
   b. activating a pressure-modifying device; and
   c. instilling a fluid or a gas into said chamber thereby increasing intrachamber pressure.

16. A method for increasing the set pressure of collapsible tubing comprising the steps of:
   a. isolating the chamber as defined by outer tubing surrounding and being secured over collapsible tubing, from ambient pressure;
   b. activating a pressure-modifying device; and
   c. evacuating air from said chamber so as to decrease intrachamber pressure.

* * * * *